United States Patent [19]

Almond et al.

[11] Patent Number: 5,298,413
[45] Date of Patent: Mar. 29, 1994

[54] ATTENUATED POLIOVIRUSES

[75] Inventors: Jeffrey W. Almond, Reading; Philip D. Minor, Potters Bar; Michael A. Skinner, Cambridge, all of United Kingdom

[73] Assignee: British Technology Group Limited, London, England

[21] Appl. No.: 62,045

[22] Filed: May 17, 1993

Related U.S. Application Data

[63] Continuation of Ser. No. 721,439, filed as PCT/GB90/00078, Jan. 18, 1990, abandoned.

[30] Foreign Application Priority Data

Jan. 18, 1989 [GB] United Kingdom ................. 8901093

[51] Int. Cl.$^5$ ........................ C12N 7/04; C12N 15/09; C12N 7/01; A61K 39/13
[52] U.S. Cl. ................................. 435/236; 435/172.3; 424/93 A
[58] Field of Search ............................. 435/236, 172.3; 424/93 A

[56] References Cited

FOREIGN PATENT DOCUMENTS

| | | | |
|---|---|---|---|
| 0323900 | 7/1989 | European Pat. Off. | C12N 7/00 |
| 0325768 | 8/1989 | European Pat. Off. | C12N 15/00 |
| 0383433 | 8/1990 | European Pat. Off. | C12N 15/41 |
| 60-207582 | 3/1986 | Japan | C12N 15/00 |

OTHER PUBLICATIONS

Kuge et al. (May 1987), J. Virol. vol. 61(5), pp. 1478-1487.
Pilipenko et al. (1989), Virology 168: 201-209.
Nomoto et al. (1982), Proc. Natl. Acad. Sci USA 79:5793-5797.
Rivera et al. (1988), Virology 165: 42-50.
La Monica et al. (1986), J. Virol. 57(2): 515-525.
Suitkin et al. (1988), Virology 166: 394-404.
Skinner et al. (1989), J. Mol. Biol. 207: 379-392.
Stanway et al. (1986), J. Virol. 57(3): 1187-1190.
Cann et al. (1984), Nucl. Acids Res. 12(20): 7787-7792.
Stanway et al. (1983), Nucl. Acids Res. 11(16): 5629-5643.
Nomoto et al. (1987), UCLA Symp. Mol. Cell. Biol. (New Series) 54:437-452.
Ren et al. (1991), J. Virol. 65(3): 1377-1382.
Almond et al. (1988), Chem. Abstracts 109, Abstract No. 228104S.
Blinov et al. (1988), Chem. Abstracts 108, Abstract No. 144367W.
P. D. Minor et al. "The effect of sequences in the 5'..." J. Gen. Virol. (1988) 69, pp. 1091-1096.
A. Z. Zelent et al. "Replicative Intermediate of..." J. Virol., 1987), (Sep. 1987), pp. 2921-2923.
A. J. Macadam et al. "The 5' noncoding region of the type..." Virology, 181(1991) pp. 451-458.
R. Ruibao et al. "Indentification of two determinants..

(List continued on next page.)

Primary Examiner—Richard A. Schwartz
Assistant Examiner—Philip W. Carter
Attorney, Agent, or Firm—Nixon & Vanderhye

[57] ABSTRACT

An attenuated enterovirus or rhinovirus, suitable for use as a vaccine, has an attenuating mutation at least at a position which is, or corresponds with, position 471 or 484 of the genome of poliovirus type 3 Leon strain.

7 Claims, No Drawings

OTHER PUBLICATIONS

." Chemical Abstracts #118401g, vol. 114 No. 13 (1991), p. 414.

Minor et al. "The effect of sequences..." J. Gen. Virol. (1988), 69, pp. 1091–1096.

Pelletier, et al. "Mutational Analysis of Upstream..." Jour. of Virol., Dec. 1988m vol. 62 No. 12, pp. 4486–4492.

Stanway, et al. "Comparison of the complete nucleotide..." Proc. Natl Acad. of Science, vol. 81 Mar. 1984, pp. 1539–1543.

Toyoda et al. "Complete nucleotide sequences..." J. Molecular Biol. 1984 vol. 124, pp. 263–270.

Biological Abstracts vol. 84 No. 107609.

Evans et al. "Increased neuvirulence..." Nature, vol. 314 Apr. 11, 1985, pp. 548–550.

Van Der Weft et al. "Synthesis of..." Proc. Natl Acad Sci vol. 83 Apr. 1986 pp. 2330–2334.

Almond et al. J. Virol. Meth, vol. 17 (1–2) (1987).

La Monica et al. J. Virol. vol. 61(9) (1987) pp. 2917–2920.

Gillis Dewalt et al. J. Virol. vol. 61(7) (1987) pp. 2162–2170.

ATTENUATED POLIOVIRUSES

This is a continuation of application Ser. No. 07/721,439, filed as PCT/GB90/00078, Jan. 18, 1990, now abandoned.

This invention relates to the construction of vaccines against rhinoviruses and enteroviruses, particularly polioviruses, by the introduction of defined mutations into their genomes. These mutations attenuate the virulence of wild type viruses and can further attenuate existing live attenuated vaccine virus strains, thereby making them less likely to revert to virulence.

At the present time, the only vaccines routinely used againt enterovirus and rhinovirus infections are those against poliomyelitis. Of these the live attenuated vaccines developed by Sabin in the 1950's have found greatest use throughout the world. Vaccine strains derived from each of the three poliovirus serotypes (Pl, P2 and P3) were prepared by passage of wild type viruses in cell cultures and whole animals until attenuated strains were obtained. These attenuated viruses are substantially less able to cause poliomyelitis in humans than the original wild type strains. They are administered orally and replicate in the gut to induce a protective immune response.

Although these vaccines are generally regarded as safe, their use is associated with a low level of paralysis in vaccinees. This is most often associated with type 2 and type 3 serotypes and rarely, if ever, with type 1. There is therefore a requirement for improved type 2 and type 3 vaccines which would be comparable in safety to the excellent type 1 strain. There is also a requirement for vaccines against other enteroviruses, e.g. echo, coxsackie and hepatitis A, and against rhinoviruses.

The Sabin vaccine strains were developed by essentially empirical procedures. The genetic basis of their attenuation is not properly understood. Over the past few years, however, scientists have employed a number of molecular biological techniques in an attempt to elucidate the mechanism by which the neurovirulence of these vaccine strains is reduced. Most of the work has concentrated on serotypes 1 and 3. For both of these the complete nucleotide sequences of the vaccine strains have been compared with those of their neurovirulent progenitors.

In the case of poliovirus type 1, the vaccine strain differs from its progenitor at 47 positions in the 7441 base genome (Nomoto et al, 1982, *Proc Natl Acad Sci USA* 79: 5793–5797). All of these are simple point mutations and 21 of them give rise to amino acid changes in virus coded proteins. Although several mutations are thought to contribute to the attenuation phenotype of the vaccine strain, direct evidence has been presented that the mutation of A to G at position 480 in the 5' non-coding region of the genome has a marked attenuating effect on the virus (Nomoto et al, 1987, *UCLA Symp Mol Cell Biol*, New Series, Vol 54, (Eds M. A. Brinton and R. R. Rueckert), 437–452, New York : Alan R Liss Inc).

Analogous studies on poliovirus type 3 reveal just 10 nucleotide sequence differences in the 7432 base genome between the vaccine and its progenitor strain (Stanway et al, 1984, *Proc Natl Acad Sci USA* 81 : 1539–1543). Just three of these give rise to amino acid substitutions in virus encoded proteins. The construction of defined recombinants between the vaccine and its progenitor strain has allowed the identification of the mutations which contribute to the attenuation phenotype. One of these is at position 2034 and causes a serine to phenylalanine change in virus protein VP3.

The other mutation of interest is C to U at position 472 in the 5' non-coding region of the genome. This-latter mutation has been observed to revert to the wild type C rapidly upon replication of the virus in the human gut (Evans et al, 1985, *Nature* 314 : 548–550). This reversion is associated with an increase in neurovirulence. C at position 472 has also been shown to be essential for growth of a mouse/human polio recombinant virus in the mouse brain (La Monica et al, 1986, *J. Virol* 57 : 515–525). Recently, we have observed that at 481 in poliovirus type 2 A changes to G in an analogous fashion upon replication of the type 2 vaccine in the gut of vaccinees.

In EP-A-0323900 attenuated enteroviruses, particularly polioviruses, and rhinoviruses are described which have an attenuating mutation at a position which is, or corresponds with, position 479 and/or 482 of poliovirus type 3 Leon strain. These attenuated viruses may also have a mutation at position 472.

We have investigated mutations at several sites approximately spanning nucleotides 470 to 540 in the 51 non-coding region of the wild-type poliovirus type 3 Leon strain. We found that poliovirus with a single mutation in the region at position 471 or 484 was attenuated but with a single mutation at position 480 was non-attenuating. Multiple mutations in the region were sometimes lethal.

The findings can be extrapolated to all polioviruses. Indeed, they may be extrapolated to other enteroviruses and rhinoviruses. Mutations at sites of other enteroviruses and rhinoviruses corresponding to position 471 and/or 484 can lead to attenuation. There is a relatively high degree of homology between the genome RNA of all enteroviruses and rhinoviruses. The positions of another strain of enterovirus or rhinovirus corresponding to positions 471 and 484 of poliovirus type 3 Leon strain (based on the numbering used in the Stanway et al paper already referred to) can be determined by lining up the sequences of the genomic RNA of the strains.

Accordingly the invention relates to attenuated enteroviruses and rhinoviruses having an attenuating mutation at least at a position which is, or corresponds with, position 471 or 484 of the genome of poliovirus type 3 Leon strain.

The present invention is particularly applicable to polioviruses. An attenuated poliovirus may be a type 1, type 2 or type 3 poliovirus. Types 2 and 3 are preferred. For types 1 and 2, positions 468 and 481 correspond to positions 471 and 484 respectively of poliovirus type 3.

We have found in particular that the mutation U to A at position 471 of the genome of poliovirus type 3 Leon strain causes attenuation, as does mutation G to A at position 484. Attenuated type 3 polioviruses may therefore contain either mutation. An attenuated type I or type 2 poliovirus may include an attenuating mutation at position 468 or 481, typically also U to A at position 468 or G to A at position 481.

An attenuated virus according to the invention is prepared by a process comprising:

(i) introducing the desired mutation by site-directed mutagenesis into a sub-cloned region, which includes the or each position it is wished to mutate, of a CDNA of an enterovirus or rhinovirus;

(ii) reintroducing the thus modified region into the complete CDNA from which the region was derived; and (iii) obtaining live virus from the CDNA thus obtained.

A mutation can be introduced into a strain of an enterovirus or rhinovirus, for example wild-type virus or a vaccine strain of virus, by site-directed mutagenesis of its genomic RNA. This may be achieved beginning with sub-cloning the appropriate region from an infectious DNA copy of the genome of any of the virus strain, for example a vaccine strain or its progenitor, into the single strand DNA of a bacteriophage such as M13. The virus strain may be a neurovirulent strain but is preferably a vaccine strain. For poliovirus it may be a Sabin, type 3 Leon or type 1 Mahoney strain. The desired mutation is then introduced into this sub-cloned CDNA using the technique of oligonucleotide directed mutagenesis.

After the introduction of mutation, the modified sub-cloned cDNAs are reintroduced into the complete CDNA from which they were derived and, for virulence testing in mice, into a CDNA derived from a murine poliovirus derivative known to cause a poliomyelitis type disease in mice (La Monica et al, 1986). Live virus is recovered from the mutated full length CDNA by production of a positive sense RNA typically using a T7 promoter to direct transcription in vitro (Van der Werf et al, 1986, *Proc Natl Acad Sci, USA* 83 : 2330–2334). The recovered RNA may be applied to tissue cultures using standard techniques (Koch, 1973, *Curr Top Microbial Immunol* 61 : 89–138). After 4–6 days incubation virus can be recovered from the supernatant of the tissue culture. The level of neurovirulence of the modified virus may then be compared with that of the unmodified virus using a standard LD50 test in mice (La Monica et al, 1986) or the WHO approved vaccine safety test in monkeys (*WHO Tech Rep Ser* 687 : 107–175, 1983).

The attenuated viruses can be used as vaccines. They may therefore be formulated as pharmaceutical compositions further comprising a pharmaceutically acceptable carrier or diluent. Any carrier or diluent conventionally used in vaccine preparations may be employed. For example, the presently used live attenuated poliovirus strains are stabilised in a solution of 1 molar $MgCl_2$ and administered as a mixture of the three serotypes.

The attenuated viruses can therefore be used to prevent an infection attributable to an enterovirus or rhinovirus in a human patient. For this purpose, they may be administered orally, as a nasal spray, or parenterally, for example by subcutaneous or intramuscular injection. A dose corresponding to the amount administered for a conventional live virus vaccine, such as up to $10^6$ $TCID_{50}$ for a Sabin vaccine strain in the case of poliovirus, may be administered.

The following Example illustrates the invention.

EXAMPLE

DNA CONSTRUCTS

A synthetic T7 polymerase promoter was cloned into pBR322 in an EcoRI - Hind3 linker to give pBRT7. The linker included a StuI site 5' of the Hinds site. The sequence from the T7 polymerase promoter to the StuI site of the resulting construct was:

TTC GAA ATT AAT ACG ACT CAC TAT AGG CCT.

This enabled sequences to be ligated to the T7 promoter so that only 2 extra G's needed to be added to the 5' end of RNA transcripts. The extreme 5' end of POLIO LEON (Stanway et al., 1984), which has a poly G tail and a Pst1 site as a result of the cDNA cloning procedure, was replaced by a linker of the sequence:

TAT GAC GCG TGC GGC CGC AAG CTT TAA $AAC_7$ . . . (polio 5' non-coding region) . . . $GGTAC_{70}$.

The 5' end was therefore limited by a Hind3 site, whilst the Pst I site and the poly G tail were removed. A KpnI site, at position 70 in Leon, was used as the 3' end of the linker. Using this construction, the 5' end of POLIO LEON from the Hind3 to a BamHI site (674), was cloned into pBRT7 to give pBRT75'L. The 5' non-coding region was brought under the control of the T7 promoter by digesting pBRT75'L with StuI and Hind3, making the Hind3 site blunt-ended using mung bean nuclease and religating to give p1-5 MBN. The resulting T7 promoter and 5' poliovirus sequence thus read:

TTCGAAATTAATACGACTCACTATAGGTTAAAAC-.

A Sst I site at the 3' end of the hybrid poliovirus type 3 leon/type 2 lansing sequence in pVN23 (Racaniello and Meriam, Virol. 155, 498–507, 1986) was removed by partial Sst I digestion, filling in by T4 polymerase and religation. Poliovirus sequences from this plasmid were then cloned into p1-5 MBN, following digestion of both plasmids with MluI and SalI, to give pT7SFP. infectious virus was recovered by linearising pT7SFP with SalI, synthesis of full length RNA using T7 polymerase and transfection of Hela cells with the RNA using the DEAE dextran method (Van der Werf et al, 1986).

The template for in vitro mutagenesis was made by subcloning the 5' non-coding region of poliovirus type 3 Leon from pVN23 (La Monica et al, 1986) into the M13 derivative of NICE (Epernon,Nucl.Acids Res.14,2830, 1986) using the Hinds and SstI sites. Mutations were then introduced into this subcloned DNA fragment using the technique of oligonucleotide-directed mutagenesis (Zoller and Smith, Nucl.Acids Res.10,64-87-6500, 1982). The chemically synthesized DNA oligonucleotides used are shown in Table I below:

TABLE 1

| Mutant | Oligonucleotide |
|---|---|
| 17 | GCA GCT GCC TG(C/T) (C/T)CC ATG GTT AG(G/A) ATT AGC CGC |
| 26 | CCA TGG TTA GGT TTA GCC GC |

Mutants were constructed by hybridising oligonucleotides to the single stranded cloned DNA fragment in the M13 phage derivative. These oligonucleotides are complementary to the target region except at the position to be mutated, where the base complementary to the desired mutation is incorporated. The hybridised M13 and oligonucleotide DNA were incubated in a reaction mixture containing DNA precursors and the enzymes DNA polymerase and DNA ligase. After incubation for one hour at 37° C., closed circular DNA was isolated from this mixture by agarose gel electrophoresis. This DNA was then used to transform *E coli* mutS or mutt (deficient in DNA mismatch repair) which were then plated out on a lawn of *E coli* JM101.

M13 plaques which arose on this lawn of *E coli* were picked and propagated and single stranded M13 phage DNA isolated. The DNAs were then sequenced using the method of Sanger and those with the desired mutation were identified. From these, batches of replicative form double stranded DNA were prepared and the mlul-Sstl fragment containing 471 base pairs of infectious poliovirus CDNA, which incorporates the mutation, was recovered.

The mutated CDNA fragment was then reintroduced into pT7SFP. Live virus was recovered from the mutated full length CDNA by the production of a positive, sense IRNA transcript from the T7 promoter in vitro (van der werf et al, 1986) which was applied to Hela cells in tissue culture using standard techniques (Koch). After 4 to 6 days incubation a cytopathic effect was observed and virus could be recovered from the supernatant.

Recovered virus was plaque purified and propagated in Hela cells. This virus pool was used for the preparation of RNA on which the sequence of the virus mutant was verified using primer extension nucleotide sequencing (Evans et al, 1985). A portion of the pool was also used to assay neurovirulence using techniques described previously.

The sequence from base 470 to 484 of the genomic RNA of poliovirus type 3 Leon strain and of mutants derived from this strain including mutants 17 and 26 is shown in Table 2 below. Mutations are shown by lower case letters. The viability of the strains is also shown, "+" meaning viable and "−" meaning not. Of the viable strains, the parental Leon strain and mutant 14 are virulent. Mutants 17 and 26 are attenuated. The LD50 for mutant 14 was $10^1$ pfu, for mutant 17 was $10^3$ pfu and for mutant 26 was $10^5$–$10^6$ pfu.

TABLE 2

| Mutant | Sequence (470–484) | Viability |
|---|---|---|
| (Leon | AUCCUAACCAUGGAG | +) |
| 1 | AauaUAACCAUGGAG | − |
| 2 | AaCaUAACCAUGGAG | − |
| 3 | AcuCUAAaaAUGagG | − |
| 11 | AUuCcUAACCAUgGGAG | − |
| 12 | AUAG | − |
| 14 | AUCCUAACCAcGGAG | + |
| 17 | AUCCUAACCAUGGAa | + |
| 26 | AaCCUAACCAUGGAG | + |

We claim:

1. An attenuated poliovirus having an attenuating mutation at least at a position which is, or corresponds with, position 471 of the genome of poliovirus type 3 Leon strain.

2. An attenuated virus according to claim 1, which is a type 1 poliovirus.

3. An attenuated virus according to claim 1, which is a type 2 poliovirus.

4. An attenuated virus according to claim 1, which is a type 3 poliovirus.

5. An attenuated virus according to claim 1, in which the base at the said position 471 or at a said corresponding position is adenine.

6. A pharmaceutical composition comprising a pharmaceutically acceptable carrier or diluent and an attenuated virus as claimed in claim 1.

7. A method of vaccinating a patient against a poliovirus, which method comprises administering thereto an effective amount of an attenuated virus as claimed in claim 1.

* * * * *